United States Patent
Lu et al.

(10) Patent No.: US 7,549,991 B2
(45) Date of Patent: Jun. 23, 2009

(54) BIPOLAR ENDOSCOPIC DEVICE WITH PARALLEL ELECTRODES FOR ENDOLUMINAL AND TRANSLUMINAL HAEMOSTASIS

(75) Inventors: Ifung Lu, Cincinnati, OH (US); Gary L. Long, Cincinnati, OH (US); Omar Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 331 days.

(21) Appl. No.: 11/436,396

(22) Filed: May 18, 2006

(65) Prior Publication Data

US 2007/0270797 A1 Nov. 22, 2007

(51) Int. Cl.
*A61B 18/14* (2006.01)
(52) U.S. Cl. .................................................. 606/50
(58) Field of Classification Search ............... 606/48–52
See application file for complete search history.

(56) References Cited

U.S. PATENT DOCUMENTS

| | | | |
|---|---|---|---|
| 4,269,174 A | 5/1981 | Adair | |
| 5,192,280 A * | 3/1993 | Parins | 606/48 |
| 5,403,311 A | 4/1995 | Abele et al. | |
| 5,720,718 A | 2/1998 | Rosen et al. | |
| 5,782,859 A * | 7/1998 | Nicholas et al. | 600/564 |
| 6,022,334 A * | 2/2000 | Edwards et al. | 604/22 |
| 6,379,349 B1 | 4/2002 | Mueller et al. | |
| 6,394,998 B1 * | 5/2002 | Wallace et al. | 606/1 |
| 6,428,538 B1 * | 8/2002 | Blewett et al. | 606/46 |
| 6,447,506 B1 | 9/2002 | Swanson et al. | |
| 6,638,275 B1 * | 10/2003 | McGaffigan et al. | 606/41 |
| 6,767,349 B2 | 7/2004 | Ouchi | |
| 6,918,906 B2 | 7/2005 | Long | |
| 6,969,389 B2 | 11/2005 | Kidooka | |
| 7,278,992 B2 * | 10/2007 | Cropper et al. | 606/41 |
| 2004/0030335 A1 * | 2/2004 | Zenati et al. | 606/51 |

FOREIGN PATENT DOCUMENTS

EP 0997108 5/2000

* cited by examiner

*Primary Examiner*—Lee S Cohen
(74) *Attorney, Agent, or Firm*—Gerry Gressel

(57) ABSTRACT

A surgical device including a shaft defining an axis and having a distal end and a proximal end, a first elongated electrode pivotally connected to the distal end of the shaft and deployable from a first configuration, wherein the first electrode is generally coaxially aligned with the axis, to a second configuration, wherein the first electrode is generally perpendicular relative to the axis, and a second elongated electrode pivotally connected to the distal end of the shaft and deployable from a first configuration, wherein the second electrode is generally coaxially aligned with the axis, to a second configuration, wherein the second electrode is generally perpendicular relative to the axis, wherein the first elongated electrode is adapted to extend radially relative to the second elongated electrode.

22 Claims, 6 Drawing Sheets

BIPOLAR ENDOSCOPIC DEVICE WITH PARALLEL ELECTRODES FOR ENDOLUMINAL AND TRANSLUMINAL HAEMOSTASIS

FIELD OF THE INVENTION

The present application relates to medical devices and systems and, more particularly, to medical devices and systems for coagulating tissue with electrical energy.

BACKGROUND OF THE INVENTION

Bleeding in the gastrointestinal ("GI") tract may be associated with various ulcers, lesions, cancers and the like. For example, peptic ulcers in the upper GI tract have been identified as a common cause of GI bleeding. If left untreated, GI bleeding may lead to anemia-like symptoms (e.g., fatigue, dizziness and chest pain), hepatic encephalopathy, hepatorenal syndrome, shock and death.

Successful treatment of GI bleeding typically includes addressing the cause of the bleeding and/or haemostasis. For example, peptic ulcers may be associated with an infection of *Helicobacter pylori* and, therefore, may require treatment of the infection to reduce the risk of re-bleeding coupled with tissue coagulation to achieve haemostasis.

Haemostasis may be achieved by invasive surgery or by various less invasive endoscopic techniques, such as laser treatment, bipolar electrocautery, heat probing, injections with sclerosing agents (e.g., epinephrine) or application of mechanical clips. While prior art endoscopic haemostasis techniques have presented some success, physicians continue to seek improved techniques for achieving haemostasis, while reducing damage to tissue adjacent to the treated tissue.

Accordingly, there is a need for an improved apparatus and system for achieving haemostasis in the GI tract.

SUMMARY OF THE INVENTION

One aspect of the disclosed surgical device includes a shaft defining an axis and having a distal end and a proximal end, a first elongated electrode pivotally connected to the distal end of the shaft and deployable from a first configuration, wherein the first electrode is generally coaxially aligned with the axis, to a second configuration, wherein the first electrode is generally perpendicular relative to the axis, and a second elongated electrode pivotally connected to the distal end of the shaft and deployable from the first configuration, wherein the second electrode is generally coaxially aligned with the axis, to the second configuration, wherein the second electrode is generally perpendicular relative to the axis, wherein the first elongated electrode is adapted to extend radially relative to the second elongated electrode.

In another aspect, the disclosed surgical system includes a shaft defining an axis and including a first wire and a second wire extending therethrough, a source of electrical energy including a first electrical connection and a second electrical connection, the first wire being electrically connected to the first electrical connection and the second wire being electrically connected to the second electrical connection, a first elongated electrode pivotally connected to the shaft and deployable from a first configuration, wherein the first electrode is generally coaxially aligned with the axis, to a second configuration, wherein the first electrode is generally perpendicular relative to the axis, the first elongated electrode being electrically connected to the first wire, and a second elongated electrode pivotally connected to the shaft and deployable from the first configuration to the second configuration, the second elongated electrode being electrically connected to the second wire, wherein the first elongated electrode is moveable relative to the second elongated electrode to grasp tissue positioned therebetween.

Other aspects of the disclosed apparatus and system will become apparent from the following description, the accompanying drawings and the appended claims.

DETAILED DESCRIPTION OF THE INVENTION

Figure 1:
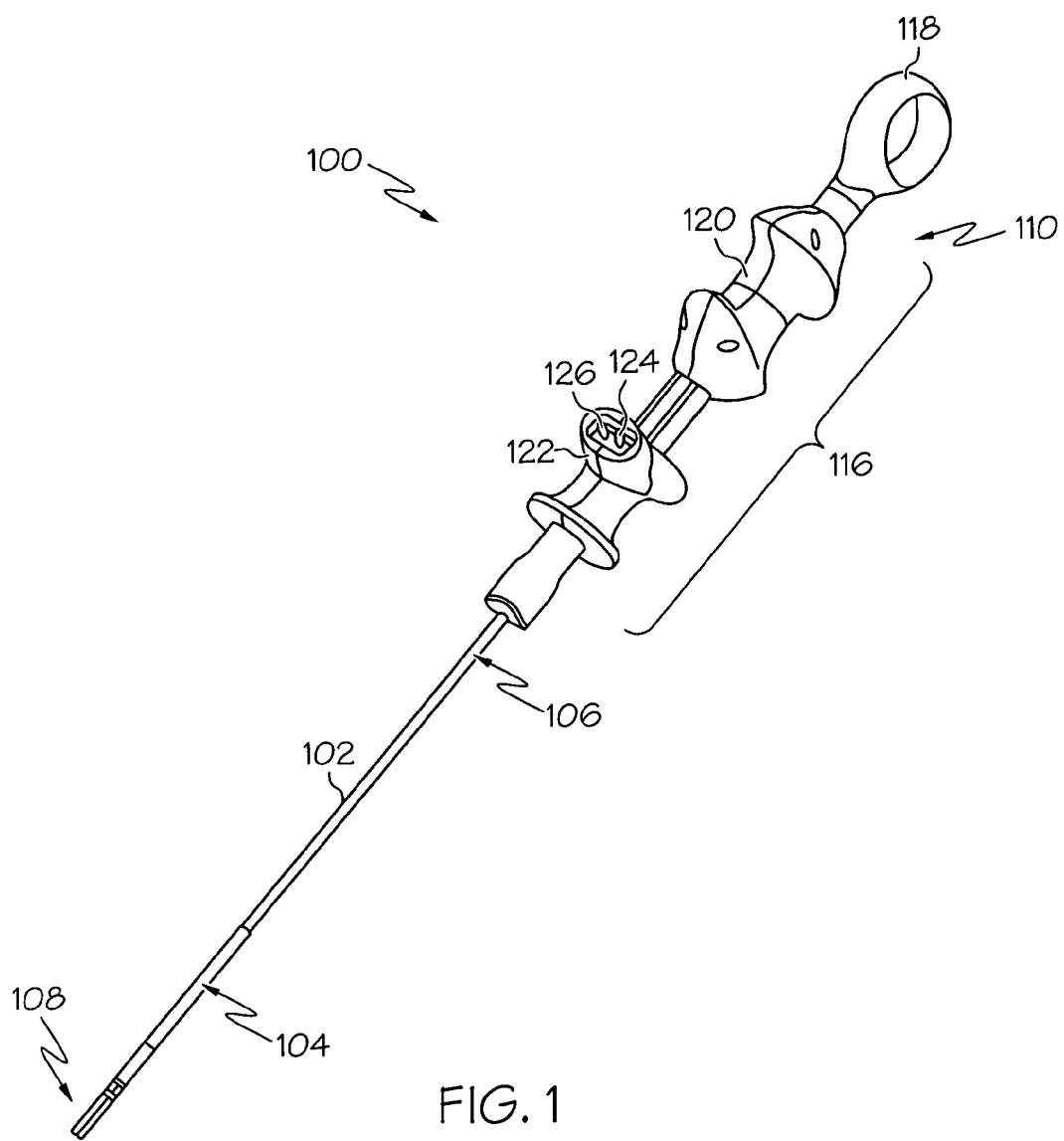
FIG. 1 is a perspective view of one aspect of the disclosed bipolar device.
Figure 6:
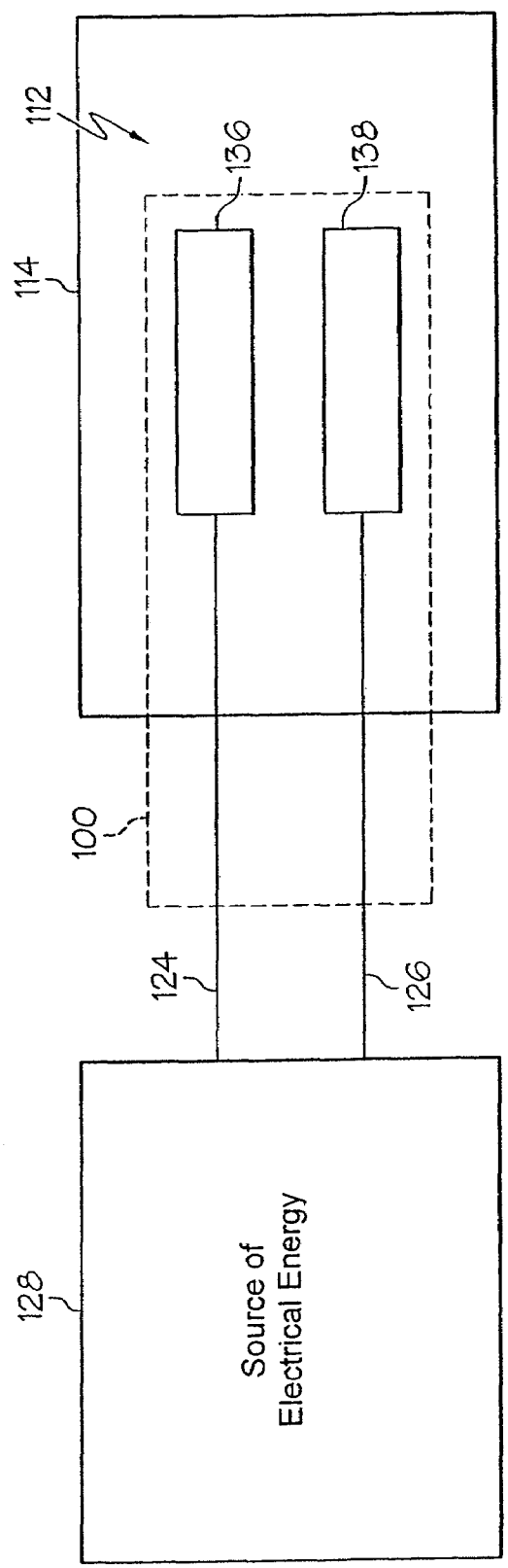
FIG. 6 is a block diagram of one aspect of a surgical system including the device of FIG. 1.

Referring to FIG. 1, one aspect of the disclosed bipolar device, generally designated 100, may include an elongated shaft 102 having a distal end 104 and a proximal end 106, a coagulation assembly 108 disposed at the distal end 104 of the shaft 102 and a handle assembly 110 disposed at the proximal end 106 of the shaft 102. The shaft 102 may be flexible and may mechanically connect the coagulation assembly 108 to the handle assembly 110. The shaft 102 and the coagulation assembly 108 may be sized and shaped to pass through a working channel 112 of an endoscope 114 (FIG. 6).

Figure 2:
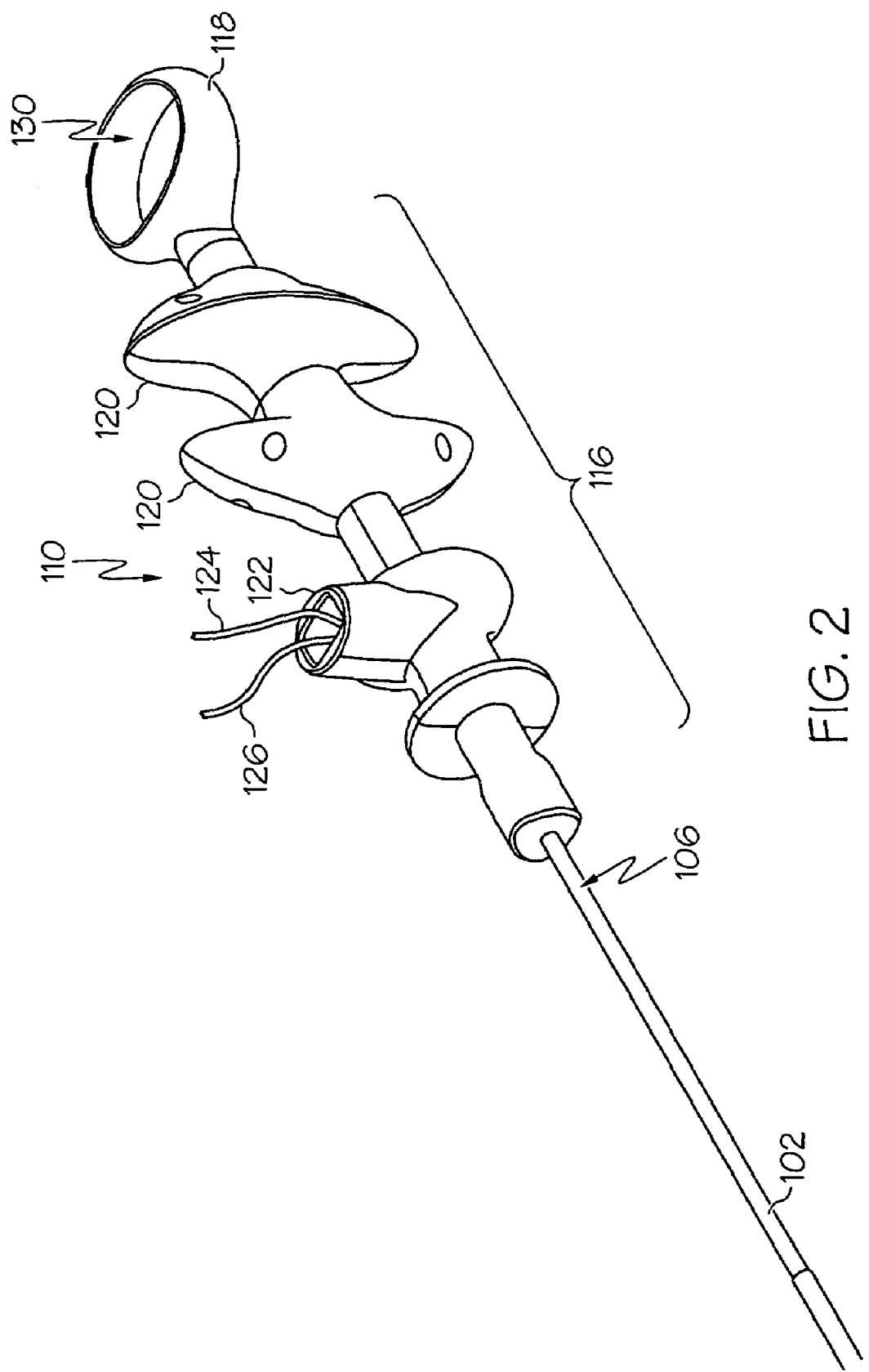
FIG. 2 is a perspective view of the handle portion of the device of FIG. 1.

As shown in FIG. 2, one aspect of the handle assembly 110 may include a base portion 116 and an actuator 118. The actuator 118 may include an opening 130 sized to receiving a finger (not shown), such as a thumb, of a user and may be connected (e.g., mechanically) to the coagulation assembly 108 to actuate the coagulation assembly 108 in response to movement of the actuator 118. The base portion 116 may include a finger gripping portion 120 and an electrical connection portion 122 including a first electrode wire 124 and a second electrode wire 126. The electrode wires 126 may extend through the shaft 102 and, as shown in FIG. 6, may connect the device 100 to a source of electrical energy (e.g., a generator) 128, such as bipolar electrical energy. The finger gripping portion 120 may allow a user to securely grasp the base portion 116 of the device 100 with, for example, a middle finger and a forefinger, while a user manipulates the actuator 118 with a thumb.

Figure 3:
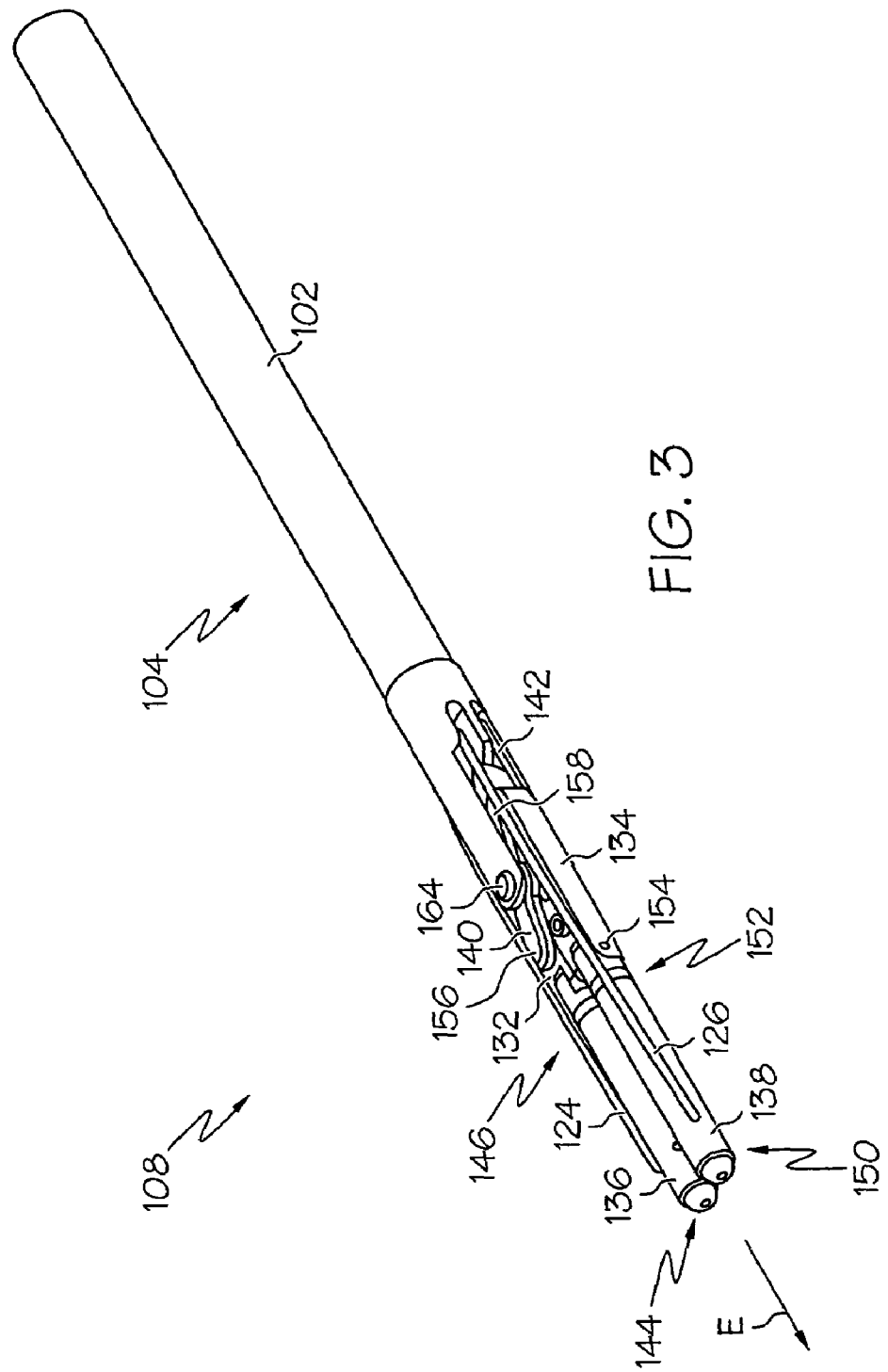
FIG. 3 is a perspective view of the working end of the device of FIG. 1 in an first, un-deployed configuration.
Figure 4:
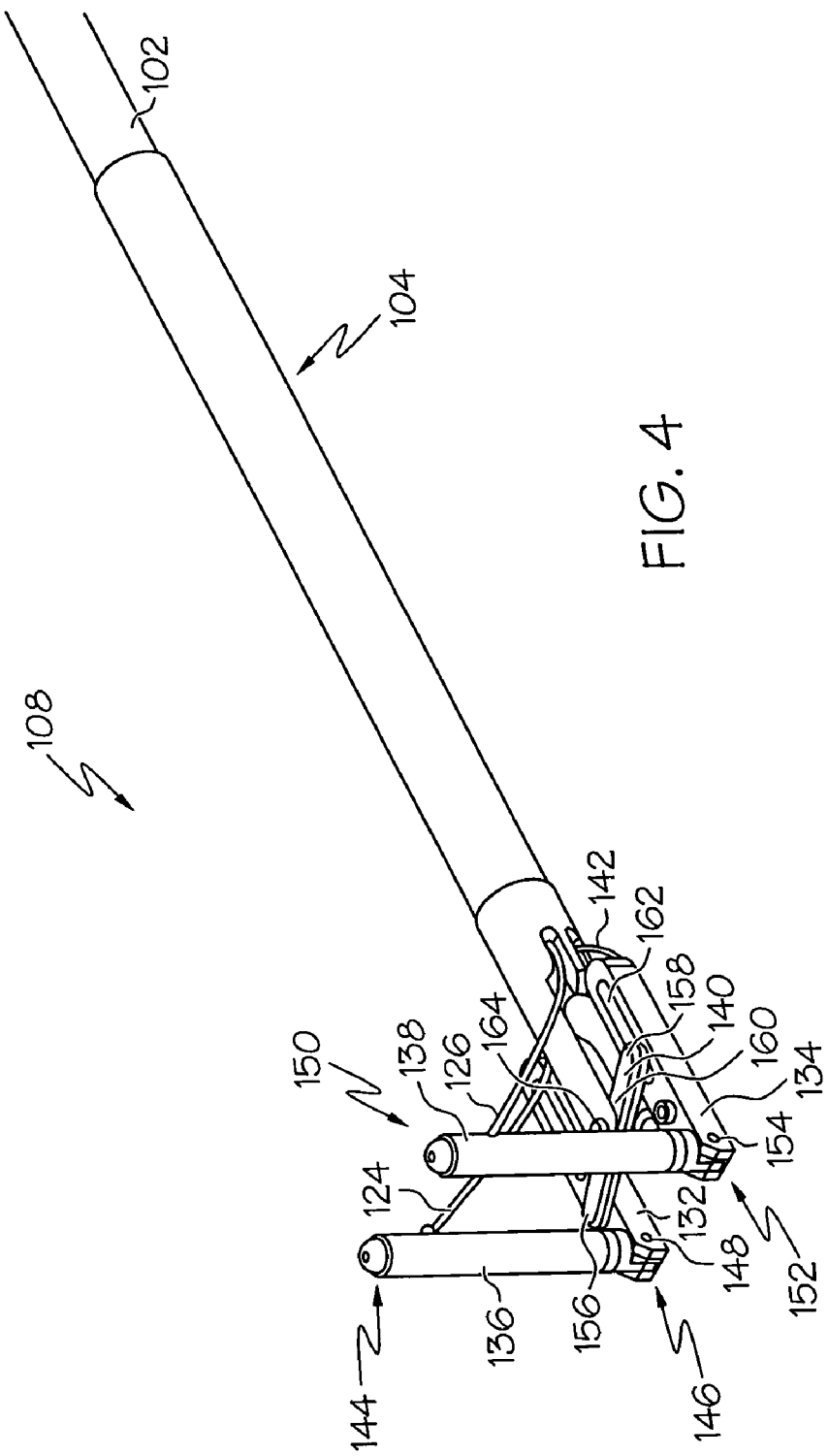
FIG. 4 is a perspective view of the device of FIG. 3 in a second, deployed configuration.
Figure 5:
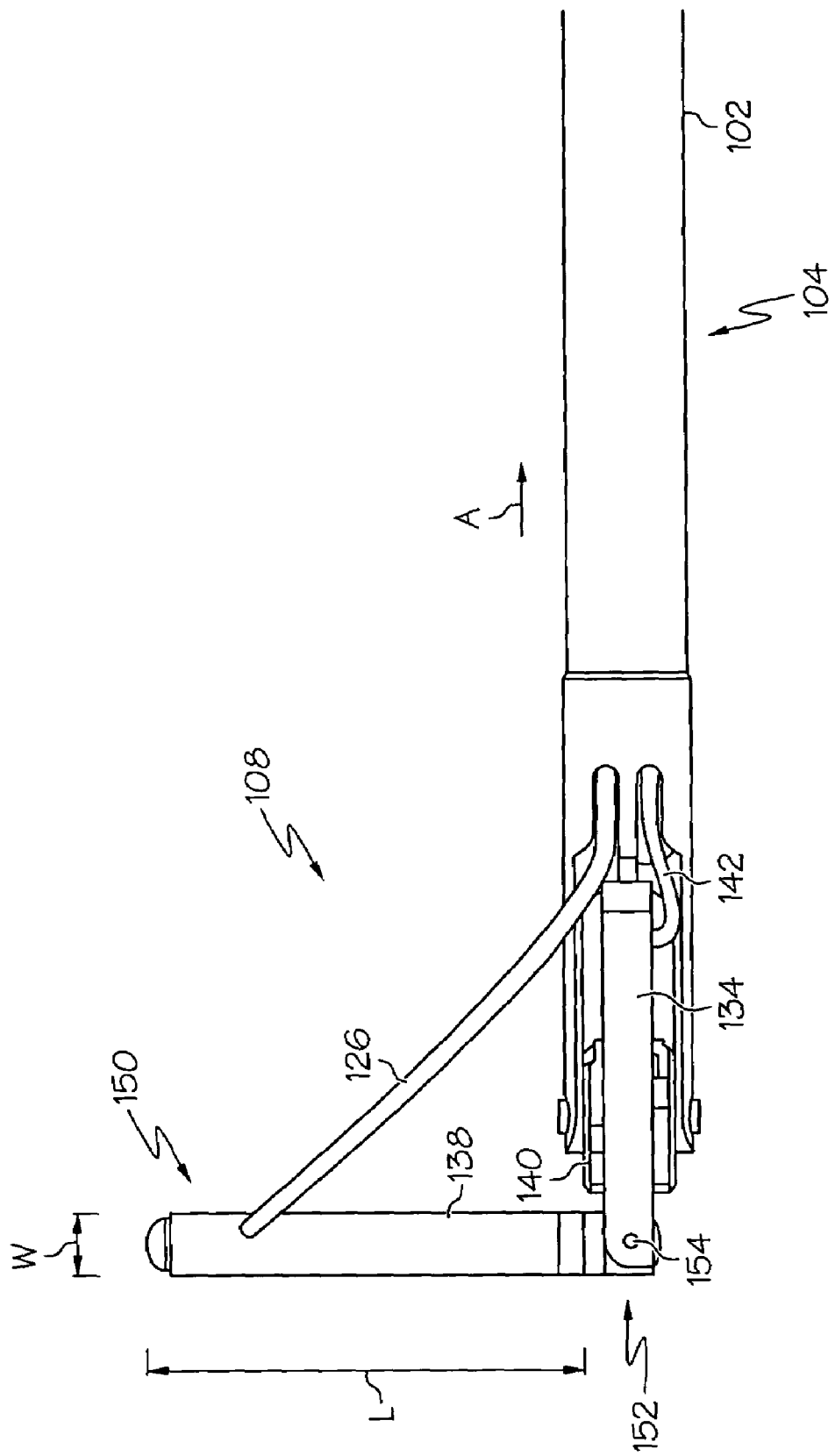
FIG. 5 is a side elevational view of the device of FIG. 4.

Referring to FIGS. 3-5, the coagulation assembly 108 may include a first arm 132, a second arm 134, a first elongated electrode 136, a second elongated electrode 138, a pivot member 140 and an actuation cable 142. The first and second elongated electrodes 136, 138 may be positioned generally parallel with respect to each other and may be formed from an electrically conductive material, such as surgical grade stainless steel, copper, gold, silver of the like.

As shown in FIG. 5, the electrodes 136, 138 may have a length L that may be generally larger than the diameter or width W. If the electrodes 136, 138 are not circular in cross-section, then the width W may refer to the width of the electrodes 136, 138 as they lay on the tissue rather than the height of the electrodes 136, 138. In one aspect, the length L may be about 1 to about 20 times the width W. In another aspect, the length L may be about 4 to about 8 times the width W.

The first elongated electrode 136 may include a distal end 144 connected to the first electrode wire 124 and a proximal end 146 pivotally connected to the first arm 132 at a pivot point 148 (e.g., a swivel joint). The second elongated electrode 138 may include a distal end 150 connected to the second electrode wire 126 and a proximal end 152 pivotally connected to the second arm 134 at a pivot point 154 (e.g., a swivel joint).

Thus, the first and/or second elongated electrodes 136, 138 may be deployed from the first (i.e., un-deployed) configuration shown in FIG. 3, wherein the electrodes 136, 136 are generally axially aligned with an elongated axis E (FIG. 3) of the shaft 102, to the second (i.e., deployed) configuration shown in FIGS. 4 and 5, wherein the electrodes 136, 138 are generally perpendicular to the elongated axis E of the shaft 102. The elongated axis E may be generally straight or may be curvilinear in response to flexing of the shaft 102.

In one aspect, the electrodes 136, 138 may be deployed by retracting the associated electrode wires 124, 126 into the shaft 102 of the device (i.e., in the direction shown by arrow A in FIG. 5), such that the electrode wires 124, 126 function as actuation cables. In another aspect, actuation cables (other than electrode wires 124, 126) may be provided for deploying the electrodes. Furthermore, those skilled in the art will appreciate that various techniques and structural arrangements may be used to achieve deployment of the electrodes 136, 138 from the first configuration to the second configuration.

Referring to FIGS. 3-5 and, in particular, to FIG. 4, the second arm 134 may include a cam slot 162 and the pivot member 140 may include a first end portion 156, a second end portion 158 and a central portion 160. The first end portion 156 of the pivot member 140 may be pivotally connected to the first arm 132, the central portion 160 may be pivotally connected to the shaft 102 at a pivot point 164 and the second end portion 158 may include a pin (not shown) slidably engaged with the cam slot 162. The actuation cable 142 may be connected to the second end portion 158 of the pivot member 140.

Thus, when the actuation cable 142 is urged in the direction shown by arrow A (FIG. 5) by, for example, actuation of the actuator 118 on the handle portion 110 of the device 100, the pivot member 140 may pivot about the pivot point 164, thereby approximating the first arm 132 towards the second arm 134 in a grasping-type action. For example, FIG. 3 shows the arms 132, 134 in a closed (i.e., grasping) configuration and FIGS. 4 and 5 show the arms 132, 134 in an open configuration. Optionally, a spring or other biasing member (not shown) may be provided to bias the first arm 132 away from the second arm 134 (i.e., to the open configuration). The grasping-type action may be performed while the electrodes 136, 138 are in the deployed and/or the un-deployed configuration.

In one aspect, the size of each electrode 136, 138, including the length L and diameter or width W, and spacing between adjacent electrodes 136, 138 may be selected to provide an Ablation Index value of about 10 to about 30, as Ablation Index is defined in U.S. Pat. No. 6,918,906 to Long, the entire contents of which are incorporated herein by reference. In another aspect, the size and spacing of each electrode 136, 138 may be selected to provide an Ablation Index value of about 10 to about 15. In another aspect, the size and spacing of each electrode 136, 138 may be selected to provide an Ablation Index value of about 13.

At this point, those skilled in the art will appreciate that by controlling the Ablation Index value of the device 100, the area of bipolar coagulation achieved by the device 100 may be limited to the area between the two electrodes 136, 138 when the electrodes are in the deployed configuration, thereby limiting undesired tissue damage.

Accordingly, the device 100 may provide a user (e.g., a physician) with a surgical tool for applying mechanical tamponade (by way of the grasping-type action described herein) and bipolar electrical energy to target tissue using moveable, generally parallel electrodes. In one aspect, a user may apply bipolar electrical energy while simultaneously using the grasping-type action for mechanical tamponade, thereby providing improved haemostasis results. In another aspect, the user may adjust the size and area of tissue treatment as desired by adjusting the spacing between the electrodes 136, 138.

Although various aspects of the disclosed apparatus and system have been shown and described, modifications may occur to those skilled in the art upon reading the specification. The present application includes such modifications and is limited only by the scope of the claims.

What is claimed is:

1. A surgical device comprising:
  a shaft defining an axis and having a distal end and a proximal end;
  a first elongated electrode connected to said distal end of said shaft at a first pivot point, said first elongated electrode being pivotable at said first pivot point from a first configuration of said first electrode, wherein said first electrode is generally coaxially aligned with said axis, to a second configuration of said first electrode, wherein said first electrode is generally perpendicular relative to said axis; and
  a second elongated electrode connected to said distal end of said shaft at a second pivot point, said second elongated electrode being pivotable at said second pivot point from a first configuration of said second electrode, wherein said second electrode is generally coaxially aligned with said axis, to a second configuration of said second electrode, wherein said second electrode is generally perpendicular relative to said axis,
  said first elongated electrode being displaceable relative to said second elongated electrode in a radial direction with respect to said axis of said shaft.

2. The device of claim 1 wherein said first and second elongated electrodes are adapted to remain generally parallel as said first and second elongated electrodes extend generally radially relative to said axis.

3. The device of claim 1 wherein said shaft is generally elongated and formed from a flexible material.

4. The device of claim 1 wherein said shaft, said first elongated electrode and said second electrode are sized to pass through a working channel of a flexible endoscope.

5. The device of claim 1 further comprising a handle assembly disposed at said proximal end of said shaft.

6. The device of claim 5 wherein said handle assembly includes an actuator connected to said first elongated electrode, said actuator being adapted to deploy said first elongated electrode to said second configuration.

7. The device of claim 1 wherein said first and second elongated electrodes are adapted to be connected to a source of electrical energy.

8. The device of claim 1 further comprising a pivot member disposed between said first and second elongated electrodes.

9. The device of claim 1 wherein at least one of said first and second elongated electrodes includes at least one of a surgical grade stainless steel, copper, gold and silver.

10. The device of claim 1 wherein each of said first and second elongated electrodes includes a length and a width, said length being larger than said width.

11. The device of claim 10 wherein said length is about 4 to about 8 times larger than said width.

12. The device of claim 1 wherein said first and second elongated electrodes are biased to a configuration wherein said first elongated electrode is generally adjacent to and not spaced from said second elongated electrode.

13. The device of claim 1 wherein said first and second elongated electrodes are sized and spaced to provide an Ablation Index value of about 10 to about 15.

14. The device of claim 1 further comprising an actuation cable connected to said first elongated electrode and extending through said shaft, wherein manipulation of said actuation cable urges said first elongated electrode from said first to said second configuration.

15. The device of claim 14 wherein said actuation cable is adapted to electrically connect said first elongated to a source of electrical energy.

16. The device of claim 1 wherein said first configuration of said first electrode and said first configuration of said second electrode are one and the same.

17. The device of claim 1 wherein said first pivot point is disposed at a proximal end of said first elongated electrode and said second pivot point is disposed at a proximal end of said second elongated electrode.

18. A surgical system comprising:
a shaft defining an axis and including a first wire and a second wire extending therethrough;
a source of bipolar electrical energy including a first electrical connection and a second electrical connection, said first wire being electrically connected to said first electrical connection and said second wire being electrically connected to said second electrical connection;
a first elongated electrode pivotally connected to said shaft at a first pivot point, said first elongated electrode being pivotable at said first pivot point from a first configuration of said first electrode, wherein said first electrode is generally coaxially aligned with said axis, to a second configuration of said first electrode, wherein said first electrode is generally perpendicular relative to said axis, said first elongated electrode being electrically connected to said first wire; and
a second elongated electrode pivotally connected to said shaft at a second pivot point, said second elongated electrode being pivotable at said second pivot point from a first configuration of said second electrode, wherein said second electrode is generally coaxially aligned with said axis, to a second configuration of said second electrode, wherein said second electrode is generally perpendicular relative to said axis, said second elongated electrode being electrically connected to said second wire,
wherein said first elongated electrode is moveable relative to said second elongated electrode to grasp tissue positioned therebetween.

19. The system of claim 18 wherein said first elongated electrode is aligned generally parallel with respect to said second elongated electrode.

20. The system of claim 18 wherein said shaft, said first elongated electrode and said second electrode are sized to pass through a working channel of a flexible endoscope.

21. The system of claim 18 wherein said first and second elongated electrodes are sized and spaced to provide an Ablation Index value of about 10 to about 15.

22. A surgical device comprising:
a shaft defining an axis and having a distal end and a proximal end;
a first elongated electrode connected to said distal end of said shaft at a first pivot point, said first elongated electrode being pivotable at said first pivot point from a first configuration of said first electrode, wherein said first electrode is generally coaxially aligned with said axis, to a second configuration of said first electrode, wherein said first electrode is generally perpendicular relative to said axis;
a second elongated electrode connected to said distal end of said shaft at a second pivot point, said second elongated electrode being pivotable at said second pivot point from a first configuration of said second electrode, wherein said second electrode is generally coaxially aligned with said axis, to a second configuration of said second electrode, wherein said second electrode is generally perpendicular relative to said axis; and
a pivot member disposed between said first and second elongated electrodes.

* * * * *

UNITED STATES PATENT AND TRADEMARK OFFICE
CERTIFICATE OF CORRECTION

| | | |
|---|---|---|
| PATENT NO. | : 7,549,991 B2 | Page 1 of 1 |
| APPLICATION NO. | : 11/436396 | |
| DATED | : June 23, 2009 | |
| INVENTOR(S) | : Lu et al. | |

It is certified that error appears in the above-identified patent and that said Letters Patent is hereby corrected as shown below:

Claim 15, Col. 5, Line 19, insert --electrode-- after "elongated"

Signed and Sealed this
Thirty-first Day of May, 2011

David J. Kappos
*Director of the United States Patent and Trademark Office*